United States Patent [19]

Kurtz et al.

[11] 4,424,155
[45] Jan. 3, 1984

[54] AMINOAZO COMPOUNDS

[75] Inventors: Walter Kurtz, Bad Durkheim; Gunther Lamm, Hassloch, both of Fed. Rep. of Germany

[73] Assignee: BASF Aktiengesellschaft, Ludwigshafen, Fed. Rep. of Germany

[21] Appl. No.: 240,316

[22] Filed: Mar. 4, 1981

[30] Foreign Application Priority Data

Mar. 15, 1980 [DE] Fed. Rep. of Germany ........... 30104

[51] Int. Cl.$^3$ ............................................. C09B 29/00
[52] U.S. Cl. ........................................................ 260/157
[58] Field of Search ........................................ 260/157

[56] References Cited

U.S. PATENT DOCUMENTS

| | | | |
|---|---|---|---|
| 4,153,343 | 5/1979 | Bloom et al. | 260/157 X |
| 4,167,394 | 11/1979 | Dehnert et al. | 260/157 X |
| 4,206,113 | 6/1980 | Dimroth et al. | 260/157 |
| 4,224,220 | 9/1980 | Lamm | 260/157 |
| 4,285,860 | 8/1981 | Hansen et al. | 260/157 X |
| 4,293,306 | 10/1981 | Hoyer et al. | 260/157 X |

FOREIGN PATENT DOCUMENTS

| | | | |
|---|---|---|---|
| 81101712.8 | 5/1982 | European Pat. Off. | 260/157 |
| 341266 | 9/1921 | Fed. Rep. of Germany | 260/157 |
| 2312087 | 9/1974 | Fed. Rep. of Germany | 260/157 |
| 1584932 | 1/1970 | France | 260/157 |
| 2154568 | 5/1973 | France | 260/157 |

*Primary Examiner*—Paul F. Shaver
*Attorney, Agent, or Firm*—Oblon, Fisher, Spivak, McClelland & Maier

[57] ABSTRACT

Aminoazo compounds of the general formula

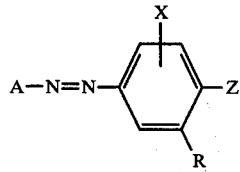

where
A is the radical of a diazo component or coupling component,
R is a radical of the formula CN, COOR$^1$, COSR$^1$, CONH$_2$, CONHNH$_2$, CONH-NH-COR$^1$,

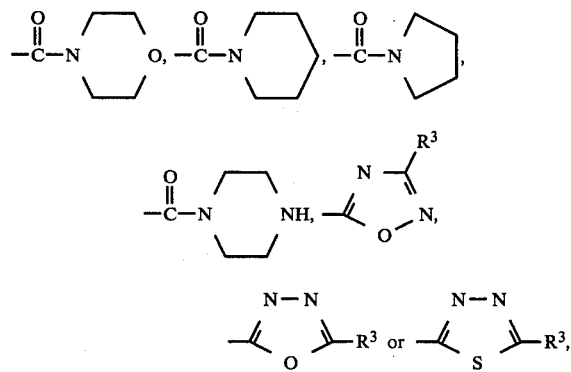

where
R$^1$ is unsubstituted or substituted alkyl, alkenyl, cycloalkyl or aryl,
R$^2$ is hydrogen or unsubstituted or substituted alkyl and
R$^3$ is hydrogen or a radical R$^1$,
Z is amino or
R and Z together are a radical of the formula —NH-CO—O—CO—,
X is hydrogen, chlorine, bromine, methoxy, ethoxy, propoxy, butoxy, phenoxy, methyl, ethyl, propyl, butyl, acetylamino, dimethylamino, diethylamino, carboxyl or —NO$_2$ and
aminobenzoic acid amides, monochloroanilines and dichloroanilines are excluded as diazo components A if R$^1$ is C$_1$—C$_4$-alkyl, methoxyethyl or butoxyethyl.

The compounds according to the invention are exceptionally suitable for use as diazo components and intermediates for the preparation of dyes.

2 Claims, No Drawings

AMINOAZO COMPOUNDS

The present invention relates to compounds of the general formula I

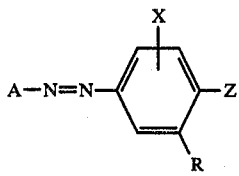

where

A is the radical of a diazo component or coupling component,

R is a radical of the formula CN, COOR$^1$, COSR$^1$, CONH$_2$, CONHNH$_2$, CONH—NH—COR$^1$,

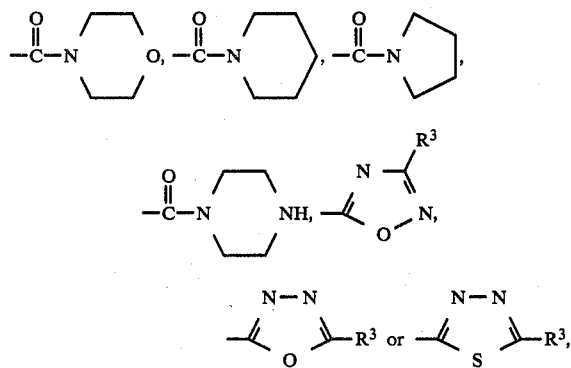

where

R$^1$ is unsubstituted or substituted alkyl, alkenyl, cycloalkyl or aryl,

R$^2$ is hydrogen or unsubstituted or substituted alkyl and

R$^3$ is hydrogen or a radical R$^1$,

Z is amino or

R and Z together are a radical of the formula —NH—CO—O—CO—,

X is hydrogen, chlorine, bromine, methoxy, ethoxy, propoxy, butoxy, phenoxy, methyl, ethyl, propyl, butyl, acetylamino, dimethylamino, diethylamino, carboxyl or —NO$_2$ and aminobenzoic acid amides, monochloroanilines and dichloroanilines are excluded as diazo components A if R$^1$ is C$_1$-C$_4$-alkyl, methoxyethyl or butoxyethoxyethyl.

The radicals A of the diazo components are in the main derived from the aniline, aminonaphthalene, aminoanthraquinone, thiazole, benzthiazole, benzisothiazole, thiadiazole, indazole, pyrazole and azobenzene series.

Examples of substituents of the radicals A of the diazo component include the following:

In the benzene series: chlorine, bromine, nitro, cyano, trifluoromethyl, methylsulfonyl, ethylsulfonyl, phenylsulfonyl, carboxyl, carbomethoxy, carbobutoxy, carbo-β-methoxy-ethoxy, carbo-β-hydroxyethoxy, unsubstituted or N-monosubstituted or N,N-disubstituted carboxamide or sulfonamide, methyl, ethyl, methoxy and ethoxy. N-Substituents of carboxamide or sulfonamide groups are, in this context, for example methyl, ethyl, propyl, butyl, β-hydroxyethyl, γ-hydroxy-propyl, β-methoxy-ethyl, γ-methoxy-propyl or γ-ethoxypropyl; alternatively, the substituted group may be a pyrrolidide, piperidide or morpholide.

In the azobenzene series: chlorine, bromine, nitro, cyano, methyl, hydroxy, ethyl, methoxy and ethoxy.

In the heterocyclic series: chlorine, bromine, nitro, cyano, methyl, ethyl, phenyl, methoxy, ethoxy, methylmercapto, β-carbomethoxy-ethylmercapto, β-carboethoxy-ethylmercapto, carbomethoxy, carboethoxy, acetyl, methylsulfonyl and ethylsulfonyl.

Specific examples of amines from which the radical A may be derived are the following: o-, m- and p-nitroaniline, o-, m- and p-cyanoaniline, 2,4-dicyanoaniline, o-, m- and p-bromoaniline, 2,4,6-tribromoaniline, 2-chloro-4-nitroaniline, 2-bromo-4-nitroaniline, 2-cyano-4-nitroaniline, 2-methylsulfonyl-4-nitroaniline, 2-methyl-4-nitroaniline, 2-methoxy-4-nitroaniline, aniline, 2-, 3- and 4-toluidine, 2-, 3- and 4-chloroaniline, 2,3- , 2,4-, 2,5-, 3,4- and 3,5-dichloroaniline, 2-methyl-4-chloroaniline, 2-methyl-5-chloroaniline, 2-methyl-3-chloroaniline, 2-, 3- and 4-trifluoromethylaniline, 2-trifluoromethyl-4-chloroaniline, 2-methyl-4,5-dichloroaniline, 3-methyl-4-chloroaniline, 3-methyl-6-chloroaniline, 3-methyl-4,6-dichloroaniline, 4-methyl-3-chloroaniline, 2-, 3- and 4-ethylaniline, 2,3-, 2,4-, 2,5-, 3,4- and 3,5-dimethylaniline, 3- and 4-acetylaminoaniline, 4-benzoylaminoaniline, 2,5-dichloro-4-acetaminoaniline, 3-acetamino-4-methylaniline, 5-acetamino-2-methylaniline, 4-acetamino-2-methylaniline, 5-chloro-4-acetylamino-2-methylaniline, 5-chloro-2-methoxyaniline, 4,5-dichloro-2-methoxyaniline, 3-chloro-4-methoxyaniline, 1-aminobenzene-4-methylsulfone, 4-aminodiphenylsulfone, 1-amino-2-chlorobenzene-4-methylsulfone, 1-amino-2-chloro-6-bromobenzene-4-methylsulfone, 4-amino-acetophenone, 3,4-dicyanoaniline, 4-aminodiphenyl ether, 4-chloro-2-nitroaniline, 4-methyl-2-nitroaniline, 4-methoxy-2-nitroaniline, 2-chloro-5-aminobenzonitrile, 2-amino-5-chlorobenzonitrile, 1-amino-2-nitrobenzene-4-sulfonic acid n-butylamide and β-methoxyethylamide, 2,4-dinitroaniline, 2,4-dinitro-6-chloroaniline, 2,4-dinitro-6-bromoaniline, 2,4-dinitro-6-cyanoaniline, 1-amino-2,4-dinitrobenzene-6-methylsulfone, 2,6-dichloro-4-nitroaniline, 2,6-dibromo-4-nitroaniline, 2-chloro-6-bromo-4-nitroaniline, 2,6-dicyano-4-nitroaniline, 2-cyano-4-nitro-6-chloroaniline, 2-cyano-4-nitro-6-bromoaniline, 1-amino-2,6-dibromo-benzene-4-methylsulfone, 1-amino-2,6-dichlorobenzene-4-methylsulfone, 1-amino-2,4-dinitrobenzene-6-carboxylic acid methyl ester and β-methoxyethyl ester, propyl 3,5-dichloroanthranilate, β-methoxyethyl 3,5-dibromoanthranilate, N-acetyl-p-phenylenediamine, methyl, ethyl, propyl, butyl, isobutyl, β-methoxyethyl, β-ethoxyethyl, methyldiglycol, ethyldiglycol, methyltriglycol, ethyltriglycol, β-hydroxyethyl, β-acetoxyethyl, β-(β'-hydroxy-ethoxy)-ethyl, β-hydroxypropyl, γ-hydroxypropyl, ω-hydroxybutyl and ω-hydroxyhexyl 2-, 3- and 4-aminobenzoate, methyl, isobutyl, methyldiglycol, β-methoxyethyl, β-butoxyethyl and β-acetoxyethyl 5-nitroanthranilate, dimethyl, diethyl, dipropyl and dibutyl 3- and 4-aminophthalate, 5-aminoisophthalate and aminoterephthalate, 3- and 4-aminobenzoic acid amide, methylamide, propylamide, butylamide, isobutylamide, cyclohexylamide, β-ethylhexylamide, γ-methoxypropylamide and γ-ethoxypropylamide, 2-, 3- and 4-aminobenzoic acid dimethylamide, diethylamide, pyrrolidide, morpholide and N-methyl-N-β-hydroxyethylamide, 5-aminoisophthalic acid diamide and bis-γ-methoxypropylamide, aminoterephthalic acid bis-diethylamide, 3- and 4-aminophthalic acid imide, β-hydroxyethylamide and γ-hydroxypropylamide, 3-amino-6-nitrophthalic acid β-hydroxyethylamide, 2-, 3- and 4-aminobenzenesulfonic acid dimethylamide, diethylamide, pyrrolidide and morpholide, 2'-, 3'- and 4'-aminophenyl methylsulfonate, 2'-, 3'- and 4'-aminophenyl ethylsulfonate, 2'-, 3'- and 4'-aminophenyl butylsulfonate, 2'-, 3'- and 4'-aminophenyl benzenesulfonate, 1- and 2-aminoanthraquinone, 1-amino-4-chloroanthraquinone, 3- and 4-aminodiphenylene oxide, 2-aminobenzthiazole, 2-aminobenzthiazole-6-carboxylic acid methyl ester, 2-amino-6-methylsulfonylbenzthiazole, 2-amino-6-cyanobenzthiazole, 2-amino-6-nitrobenzthiazole, 5,6- and 6,7-dichloro-2-aminobenzthiazole, 4-amino-5-bromo-7-nitro-1,2-benzisothiazole, 3-amino-5-nitro-2,1-benzisothiazole, 3-amino-5-nitro-7-bromo-2,1-benzisothiazole, 2-aminothiazole, 2-amino-5-nitrothiazole, 2-amino-4-methylthiazole-5-carboxylic acid ethyl ester, 2-amino-4-methyl-5-acetylthiazole, 2-amino-3-cyano-4-methylthiophene-5-carboxylic acid (methyl, ethyl, propyl or butyl) ester, 2-phenyl-5-amino-1,3,4-thiadiazole, 3-methylmercapto-5-amino-1,2,4-thiadiazole, 3-β-carbomethoxyethylmercapto-5-amino-1,2,4-thiadiazole and the diazo components of the formulae

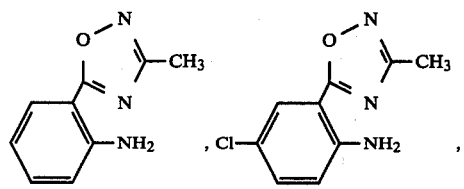

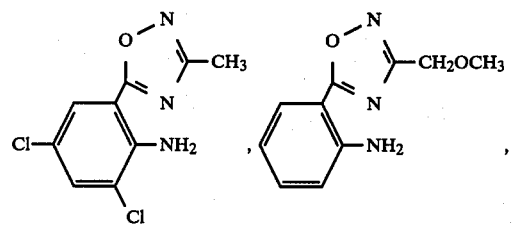

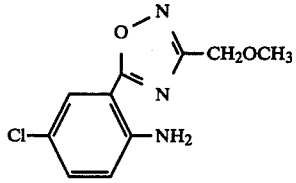

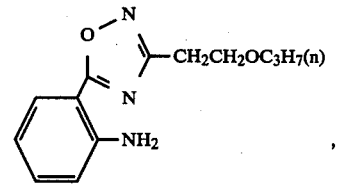

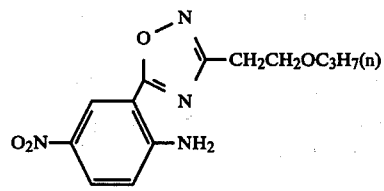

-continued

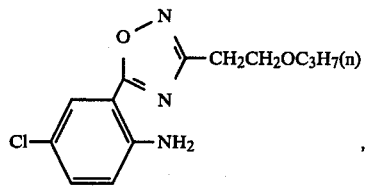

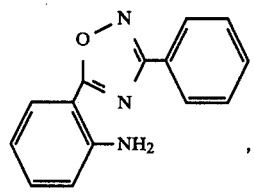

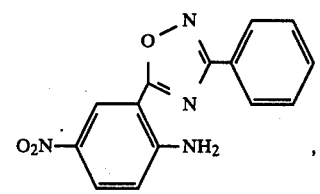

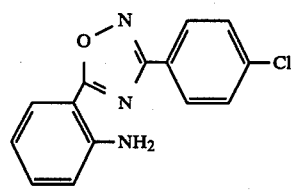

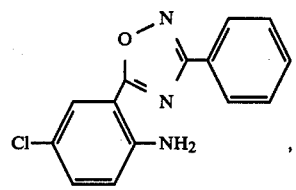

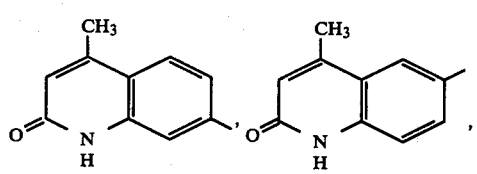

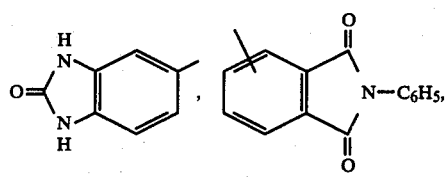

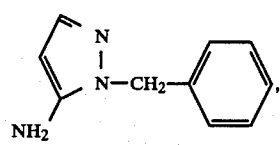

-continued

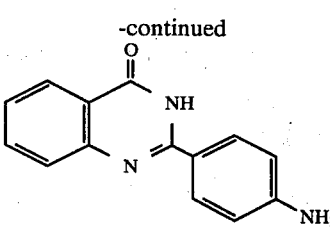

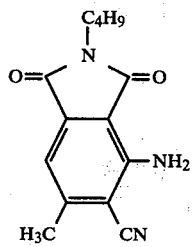

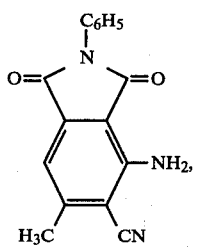

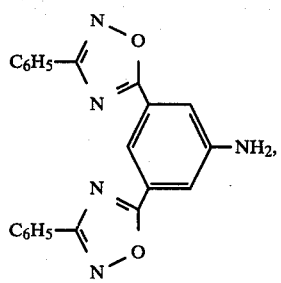

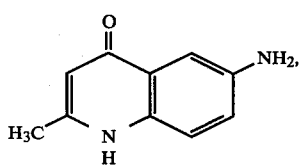

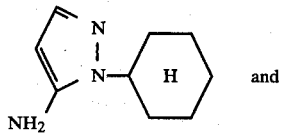

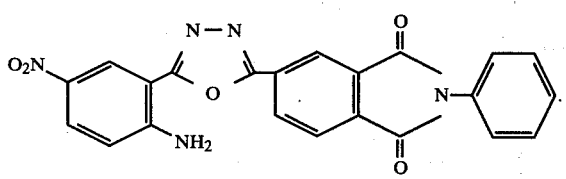

Examples of suitable diazo components A-NH₂ of the aminoazobenzene series are: 4-aminoazobenzene, 2',3-dimethyl-4-aminoazobenzene, 3',2-dimethyl-4-aminoazobenzene, 2,5-dimethyl-4-aminoazobenzene, 2-methyl-5-methoxy-4-aminoazobenzene, 2-methyl-4',5-dimethoxy-4-aminoazobenzene, 4'-chloro-2-methyl-5-methoxy-4-aminoazobenzene, 4'-nitro-2-methyl-5-methoxy-4-aminoazobenzene, 4'-chloro-2-methyl-4-aminoazobenzene, 2,5-dimethoxy-4-aminoazobenzene, 4'-chloro-2,5-dimethoxy-4-aminoazobenzene, 4'-nitro-2,5-dimethoxy-4-aminoazobenzene, 4'-chloro-2,5-dimethyl-4-aminoazobenzene, 4'-methoxy-2,5-dimethyl-4-aminoazobenzene, 4'-nitro-4-aminoazobenzene, 3,5-dibromo-4-aminoazobenzene, 2,3'-dichloro-4-aminoazobenzene, 3-methoxy-4-aminoazobenzene, 4'-hydroxy-2'-methyl-4-aminoazobenzene and 3-chloro-4-aminoazobenzene.

Specific examples of particularly valuable diazo components A-NH₂ are: 4-nitroaniline, 2-chloro-4-nitroaniline, 2-bromo-4-nitroaniline, 2-cyano-4-nitroaniline, 2-methoxy-4-nitroaniline, 2-amino-5-nitrophenylsulfonic acid dimethylamide, 2-amino-5-nitrophenylsulfonic acid butylamide, 2-amino-5-nitrophenylsulfonic acid β-methoxyethylamide, 2-aminobenzonitrile, 2-chloro-4-aminobenzonitrile, 2-chloro-5-aminobenzonitrile, 2-amino-5-chlorobenzonitrile, 3,5-dichloro-2-aminobenzonitrile, 1-amino-2,4-dicyanobenzene, 1-amino-2,4-dicyano-6-chlorobenzene, 2-chloro-4-amino-5-nitrobenzonitrile, 2-amino-3-chloro-5-nitrobenzonitrile, 2-amino-3-bromo-5-nitrobenzonitrile, 2,6-dicyano-4-nitroaniline, 2,5-dichloro-4-nitroaniline, 2,6-dichloro-4-nitroaniline, 2,6-dibromo-4-nitroaniline, 2-chloro-6-bromo-4-nitroaniline, 2,4-dinitroaniline, 2,4-dinitro-6-chloroaniline, 2,4-dinitro-6-bromoaniline, 2-amino-3,5-dinitrobenzonitrile, 1-amino-4-nitrobenzene-2-methylsulfone, 1-amino-4-nitrobenzene-2-ethylsulfone, 4-methylsulfonylaniline, 1-amino-2-chlorobenzene-4-methylsulfone, 1-amino-2,6-dibromobenzene-4-methylsulfone, 1-amino-2,6-dichlorobenzene-4-methylsulfone, 2-(3'-phenyl-1,2,4-oxdiazolyl)-aniline, 2-(3'-methoxymethyl-1,2,4-oxdiazolyl)-aniline, o-, m- and p-chloroaniline, o-, m- and p-bromoaniline, methyl, ethyl, propyl and methoxyethyl anthranilate, 2- and 4-aminobenzoic acid esters, 2-amino-5-nitrobenzoic acid esters, 2-amino-3-chloro-5-nitrobenzoic acid esters, 2-amino-3,5-dichlorobenzoic acid esters, 2-amino-3,5-dibromobenzoic acid esters, methyl and β-methoxyethyl 2-amino-3,5-dinitrobenzoate, diethyl 2-aminoterephthalate, 4-aminoazobenzene, 2,3'-dimethyl-4-aminoazobenzene, 2',3-dimethyl-4-aminoazobenzene, 2,5-dimethyl-4-aminoazobenzene, 3,5-dibromo-4-aminoazobenzene, 3-chloro-4-aminoazobenzene, 3-bromo-4-aminoazobenzene, p-cyanoaniline, 2,6-dicyano-4-chloroaniline, 2,6-dicyano-4-methylaniline and 2,6-dichloro-4-cyanoaniline.

Examples of particularly valuable heterocyclic diazo components A-NH₂ are 2-aminothiazole, 2-amino-5-nitrothiazole, 2-amino-4-methylthiazole-5-carboxylic acid ethyl ester, 2-amino-5-phenyl-1,3,4-thiadiazole, 3-phenyl-5-amino-1,2,4-thiadiazole, 3-methylmercapto-5-amino-1,2,4-thiadiazole, 3-β-carbomethoxyethylmercapto-5-amino-1,2,4-thiadiazole, 3-β-carboethoxyethylmercapto-5-amino-1,2,4-thiadiazole, 2-amino-6-cyanobenzthiazole, 2-aminobenzthiazole-6-carboxylic acid methyl ester, 2-amino-6-nitrobenzthiazole, 2-amino-3-cyano-4-methylthiophene-5-carboxylic acid esters, 1-benzyl-5-aminopyrazole and 1-cyclohexyl-5-aminopyrazole.

Coupling component radicals A may be derived, for example, from the phenol, naphthalene, pyridone, pyrazolone, pyridine, pyrimidine, acetoacetanilide, indole, thiazole, homophthalimide and aniline series.

Some specific examples are phenol, o-, m- and p-cresol, 2,6-dihydroxy-4-methylpyridine, 2,6-dihydroxy- 3-cyano-4-methylpyridine, 1,4-dimethyl-2-hydroxy-3-cyanopyrid-6-one, 1-ethyl-2-hydroxy-3-cyano-4-methylpyrid-6-one, 2-aminonaphthalene-1-sulfonic acid, 1-hydroxynaphthalene, 2-hydroxynaphthalene, 2-naphthol-3-carboxylic acid phenylamide, 2-naphthol-3-carboxylic acid anisidide, 3-phenyl-5-diethylaminothiazole, acetoacetic acid dianisidide, phenylindole, methylindole, 1-phenyl-3-methylpyrazol-5-one and 1-phenyl-3-carbo-$C_1$-$C_4$-alkoxypyrazol-5-one.

Specific examples of radicals R of the formula $COOR^1$ are: $COOCH_3$, $COOC_2H_5$, $COOCH(CH_3)_2$, $COOC_3H_7(n)$,

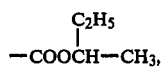

$COOC_4H_9(n)$, $COOC_5H_{11}$, $COOC_6H_{13}(n)$, $COOC_6H_{13}(i)$,

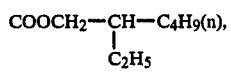

$COOC_9H_{19}(n)$, $COOC_{10}H_{21}(n)$, $COOC_{10}H_{21}(i)$, $COOCH_2CH_2OCH_3$, $COOCH_2CH_2OC_2H_5$, $COOCH_2CH_2OC_4H_9(n)$,

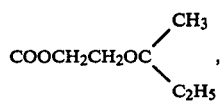

$CO(OCH_2CH_2)_2OCH_3$, $CO(OCH_2CH_2)_2OC_4H_9(n)$, $CO(OCH_2CH_2)_3OCH_3$, $CO(OCH_2CH_2)_3OC_4H_9(n)$, $CO(OCH_2CH_2)_4OCH_3$, $CO(OCH_2CH_2)_4OC_4H_9(i)$, $CO(OCH_2CH)_2OCH_3$, $CO(OCHCH_2)_2OCH_3$, $COOCHCH=CH_2$,
$\quad\quad\quad |\quad\quad\quad\quad\quad\quad |\quad\quad\quad\quad\quad\quad\quad |$
$\quad\quad\quad CH_3\quad\quad\quad\quad\quad CH_3\quad\quad\quad\quad\quad CH_3$

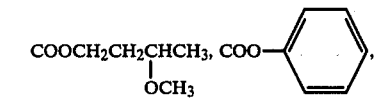

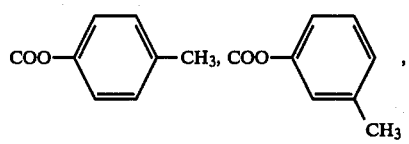

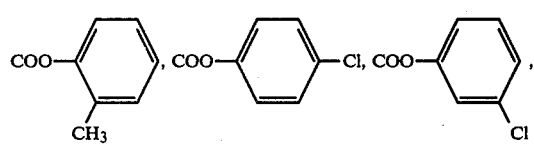

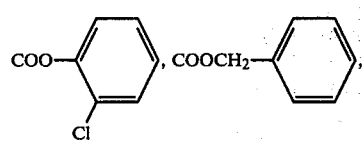

-continued

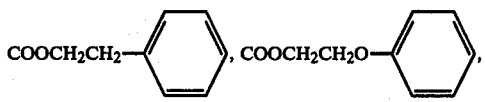

$COOCH_2CH_2OCOCH_3$, $COOCH_2CH_2NHCOCH_3$ and $COO(CH_2)_3NH—COCH_3$.

Examples of radicals $R^3$ on the heterocyclic radicals

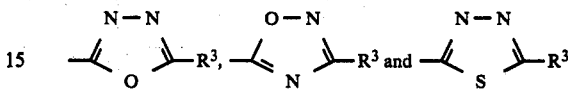

are hydrogen, $C_1$-$C_8$-alkyl which may or may not be interrupted by oxygen and substituted by hydroxyl, pyrrolidonyl, phthalimidyl, $C_1$-$C_8$-alkoxy, allyloxy, benzyloxy, phenylethoxy, phenoxy, methylphenoxy, chlorophenoxy or methoxyphenoxy, benzyl, phenylethyl, cyclohexyl, phenyl which may or may not be substituted by chlorine, bromine, nitro, methyl, ethyl, methoxy or ethoxy, naphthyl, pyridyl, thienyl and furyl.

Specific examples of radicals $R^3$ on the heterocyclic radicals are methyl, ethyl, propyl, butyl, pentyl, hexyl, heptyl, 1-ethylpentyl, methoxymethyl, methoxyethyl, n-propoxyethyl, i-propoxyethyl, n-butoxyethyl, n-hexoxyethyl, phenyl, phenylallyl and radicals of the formulae

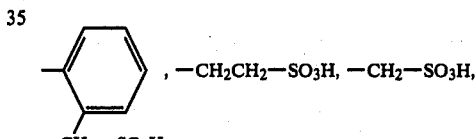

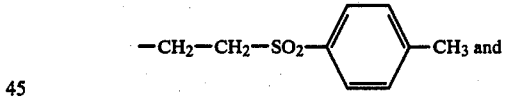

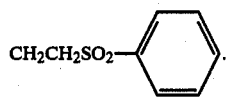

The compounds of the formula I, where A is the radical of a diazo component, may be prepared by coupling a diazo compound of an amine of the formula

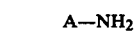

A—NH$_2$ with a compound of the formula

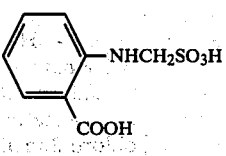

then splitting off again the radical $CH_2SO_3H$ and converting the COOH group to a radical of the formula R.

The compounds of the formula I, where A is the radical of a coupling component, may be prepared by coupling a compound of the formula

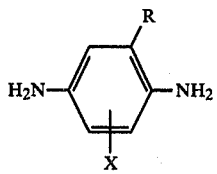

with a compound of the formula

AH

The processes are known in principle. Details of the preparation of the compounds may be found in the Examples, where parts and percentages are by weight, unless stated otherwise.

The compounds of the formula I are valuable diazo components for the preparation of azo dyes, to which they are converted by diazotization followed by coupling with coupling components.

Compounds of particular importance are those of the formula I a

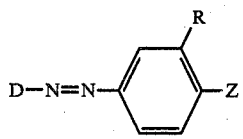

where

D is the radical of a diazo component and
Z and R have the stated meanings.

Preferred diazo components are derived from the aniline, phthalimidyl, quinazolonyl, pyrazole and thiazole series, suitable substituents for the diazo components being, in particular, fluorine, chlorine, bromine, trifluoromethyl, methyl, ethyl, methoxy, ethoxy, phenoxy, cyano, nitro, methylsulfonyl, ethylsulfonyl, allylsulfonyl, phenylsulfonyl, carboxyl, carboxylic acid ester groups, unsubstituted and substituted sulfamyl and oxdiazolyl.

Preferred radicals R are

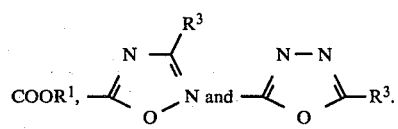

Examples of preferred radicals $R^1$ are $COOCH_3$, $COOC_2H_5$, $COOC_3H_7(n)$, $COOC_3H_7(i)$, $COOC_4H_9(n)$,

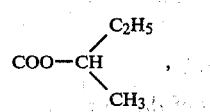

$COOC_5H_{11}$, $COOC_6H_{13}(n)$, $COOC_6H_{13}(i)$, $COOC_8H_{17}(n)$,

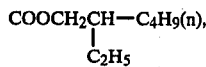

$COOC_9H_{19}(n)$, $COOC_{10}H_{21}(n)$, $COOC_{10}H_{21}(i)$, $COOCH_2CH_2OCH_3$, $COOCH_2CH_2OC_4H_9$, $CO(OCH_2CH_2)_2OCH_3$, $CO(OCH_2CH_2)_2OC_2H_5$, $CO(OCH_2CH_2)_2OC_4H_9(n)$, $CO(OCH_2CH_2)_3OCH_3$, $CO(OCH_2CH_2)_3OC_4H_9$, $CO(OCH_2CH_2)_4OCH_3$, $CO(OCH_2CH_2)_4OC_4H_9$,

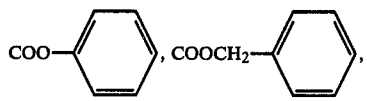

$CON(CH_3)_2$, $CON(C_2H_5)_2$ and $CONH_2$.

Examples of preferred radicals $R^3$ in the 1,2,4-oxdiazolyl series are $CH_3$, $C_2H_5$, $CH_2OCH_3$, $CH_2CH_2OCH_3$, $CH_2CH_2OC_2H_5$, $CH_2CH_2OC_3H_7(n)$, $(CH_2CH_2O)_2CH_3$, $(CH_2CH_2O)_3CH_3$, $(CH_2CH_2O)_2C_3H_7(n)$, $C_6H_5$, $C_6H_4CH_3$ and $C_6H_4Cl$.

Examples of preferred radicals $R^3$ in the 1,3,4-oxdiazolyl series are $CH_3$, $C_2H_5$, $C_3H_7$, $C_5H_{11}(n)$,

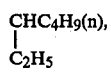

$C_6H_{13}$ and $C_6H_5$.

EXAMPLE 1

127.5 parts of 3-chloroaniline are diazotized in a conventional manner in an aqueous medium. After destroying the excess nitrous acid with amidosulfonic acid, the diazonium salt solution is buffered, for example with sodium bicarbonate, to pH 5.0–6.0, and a solution of 232 parts of the compound of the formula

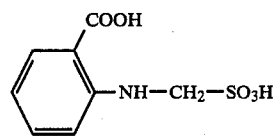

in 750 parts by volume of water is then added. The coupling mixture is stirred overnight at pH 4.5–6.0; this completes the reaction. The pH of the mixture is then raised to 10.0–11.0 by adding 80 parts of 50% strength sodium hydroxide solution and the mixture is heated to 80° C., a further total of 80 parts of 50% strength sodium hydroxide solution being added to stop the pH from falling below 9.8. The elimination of the methanesulfonic acid group is complete after about 3 hours. The product which has precipitated is filtered off. The filter residue is stirred with 1,000 parts by volume of water, acidified to pH 5.0–7.5 with hydrochloric acid, and again filtered off. After washing with water and drying, 240 parts of a yellowish brown powder of the formula

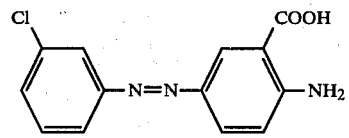

are obtained; this material dissolves completely in acetone, and melts at 230°–235° C.

Ultraviolet spectrum: $\lambda_{max}$: 371 nm
in glacial acetic acid.

455 parts of 4-amino-3′-chloroazobenzene-3-carboxylic acid are suspended in 2,000 parts by volume of nitrobenzene. Phosgene is passed into the suspension for 5 hours at 90°–95° C., the excess phosgene is then removed from the reaction mixture by blowing air through the latter, and the product which has precipitated, and has the formula

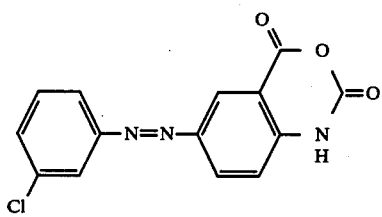

is filtered off, washed with cyclohexane and dried. 360 parts of a brown powder of melting point >150° C. are obtained.

Determination of Cl: found 12.5%; theory 11.8%.

150 parts of the compound thus obtained, 350 parts by volume of N-methylpyrrolidone and 72 parts of 2-ethylhexanol are heated to 80° C. 15 parts by volume of triethylamine are then added dropwise and the mixture is stirred for 4 hours at 110° C. When it has cooled, 1,000 parts by volume of water are run in slowly, with thorough stirring, and the product which has precipitated, and has the formula

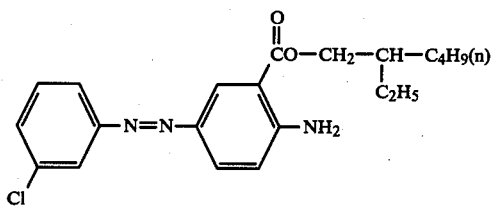

is filtered off, washed with water and dried. 180 parts of a golden yellow powder, melting at 93°–96° C., are obtained.

Ultraviolet spectrum: $\lambda_{max}$: 370 nm
Shoulder at 349 nm
Solvent: glacial acetic acid.

EXAMPLE 2

500 parts of the compound of the formula

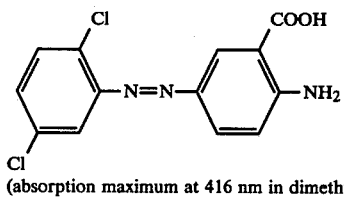

(absorption maximum at 416 nm in dimethylformamide)

(the compound being prepared by a process similar to that described in Example 1) are phosgenated by a method similar to that described in Example 1. 510 parts of the compound of the formula

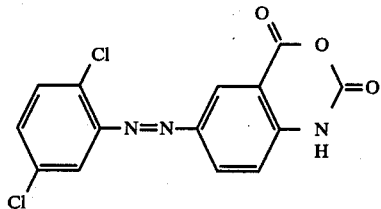

are obtained; melting point 327° C.

200 parts by volume of acetone are added to 100 parts of this product and the mixture is combined with 1,000 parts of 25% strength aqueous ammonia. The mixture is stirred for 1 hour at 50° C. and the product is then filtered off and washed with water. After drying, 78 parts of the product of the formula

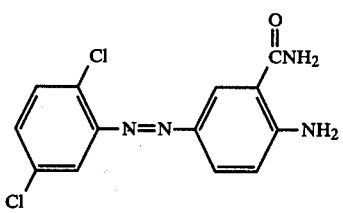

are obtained; melting point 232° C.

Infrared spectrum: very strong absorption bands at 1,595 and 1,623 cm$^{-1}$.

72 parts of this product are dissolved in 240 parts of dimethylformamide and the mixture is added to a solution of 60 parts of phosgene in 160 parts of dimethylformamide. The mixture is stirred for a further hour at 40° C. and, when it has cooled, is stirred into 300 parts of water. The resulting suspension is buffered to a pH of 7–8 with sodium hydroxide solution. The product which has precipitated is filtered off and washed; 75 parts of a yellow powder of the formula

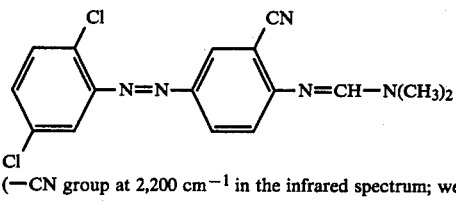

(—CN group at 2,200 cm$^{-1}$ in the infrared spectrum; weak)

are isolated. The product does not have a sharp melting point and sinters at from 160° to 250° C. 400 parts by volume of methanol, 80 parts of concentrated sulfuric acid and 50 parts of water are added to 70 parts of the above product. The mixture is stirred under reflux for 8 hours, 3,000 parts of water are then added and the precipitate is neutralized to pH 3.5–4.5 with sodium hydroxide solution. The product is filtered off hot and washed with water. 60 parts of 2′,5′-dichloro-3-cyano-4-aminoazobenzene of melting point 250° C. are obtained. In the spectrophotometric infrared recording, the cyano group shows up, to a moderately pronounced degree, at 2,195 cm$^{-1}$.

EXAMPLE 3

If 100 parts of the compounds of the formula

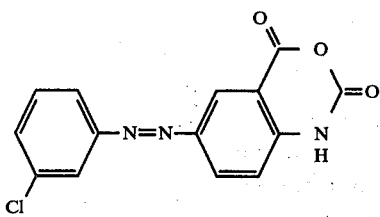

are reacted with ammonia by a method similar to that described in Example 2, 74 parts of 3'-chloro-3-carbamyl-4-aminoazobenzene are obtained (melting point: 252° C.; infrared spectrum: very strong, split absorption band at 1,591 cm$^{-1}$ and 1,619 cm$^{-1}$).

Dehydration (for example by a method similar to that described in Example 2) of the above product gives 66 parts of 3'-chloro-3-cyano-4-aminoazobenzene, of melting point 255° C. (infrared spectrum: —CN band at 2,190 cm$^{-1}$ (weak); further, strong absorption bands at, for example, 1,685 cm$^{-1}$ and 1,589 cm$^{-1}$ (carrier: KBr)).

EXAMPLE 4

353 parts of ethyl 4-aminobenzoate are diazotized in a conventional manner, in about 2,000 parts by volume of water, by means of hydrochloric acid and sodium nitrite, with addition of ice. After removing excess nitrous acid, the diazonium salt solution is run into a solution of 445 parts of the compound of the formula

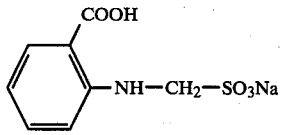

in 1,500 parts by volume of water at 0°–10° C., the pH of the coupling component solution having first been buffered to 4.5–6.0. Whilst running in the diazonium salt solution, the coupling mixture is kept at pH 4.5–6.0 (for example by adding solid sodium bicarbonate, sodium carbonate or dilute sodium hydroxide solution). The coupling mixture is stirred for a further 10 hours, during which time it rises to room temperature. The mixture is then heated to 70°–90° C. and concentrated sodium hydroxide solution is added, following a procedure similar to that described in Example 1, so that the protective group is split off in the course of 3–4 hours at a pH of from 10 to about 13. The mixture is then allowed to cool and is acidified to pH 4–5 with hydrochloric acid, and the product is filtered off, washed and dried.

495 parts of a dark yellow product of the formula

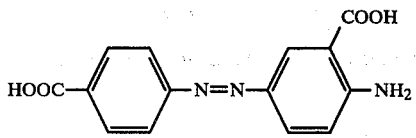

are obtained; this decomposes on heating at 260° C. A yellow solution of 0.01 part of this product in 1,000 parts by volume of dimethylformamide has an absorption maximum at 407.5 nanometers (nm).

373 parts of this product are suspended in 1,000 parts by volume of nitrobenzene and 15 parts of tetrahydrofuran. Phosgene is then passed in, at 40°–70° C., until the reaction is complete (which requires 3–6 hours). After blowing out excess phosgene, the product which has precipitated is filtered off and washed with cyclohexane. After drying, 446 parts of the compound of the formula

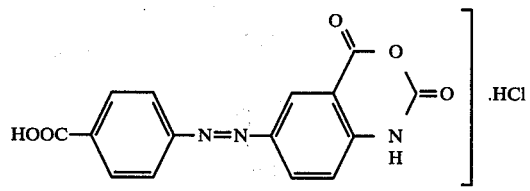

are obtained as a brown powder, of melting point 132° C.

100 parts of this compound are reacted with 300 parts of n-propanol by a method similar to that described in Example 1. After isolating and drying the product in a conventional manner, a yellow powder of the formula

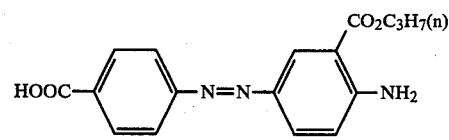

is obtained; this gives a pale yellow solution in dimethylformamide and has an absorption maximum of 401 nm.

EXAMPLE 5

121 parts of the product of the formula

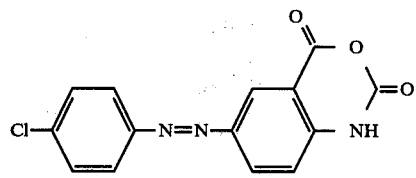

are suspended in 400 parts by volume of N-methylpyrrolidone. 60 parts of 2-phenoxyethanol are then added, the mixture is heated to 50°–80° C., and 5 parts of triethylamine are introduced dropwise. The mixture is stirred for 2–3 hours, until the reaction is complete, and is then cooled to room temperature, and the reaction product is precipitated with water.

After filtering off, washing with water and drying, 148 parts of the diazo component of the formula

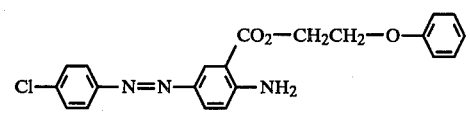

are obtained as a yellowish brown powder, which melts at 140° C.

EXAMPLE 6

150 parts of the compound of the formula

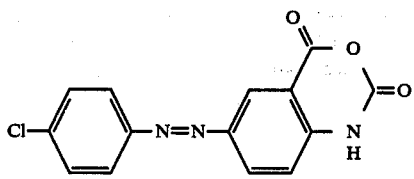

are treated with 800 parts of methanol and 20 parts by volume of triethylamine, by a method similar to that described in Example 1. 141 parts of the compound of the formula

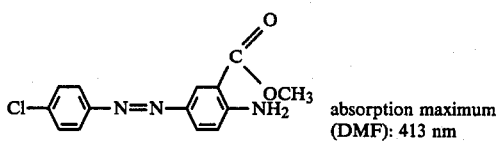 absorption maximum (DMF): 413 nm are obtained as a yellow powder melting at 208°-210° C.

140 parts of the same compound are obtained if instead of triethylamine 27 parts of sodium methylate in 80 parts by volume of methanol are added, and in other respects the same procedure is followed.

EXAMPLE 7

353 parts of ethyl 4-aminobenzoate are coupled, by a method similar to that described in Example 5, with 4'-carboxyethyl-3-carboxyl-azobenzene-4-amino-ω-methanesulfonic acid

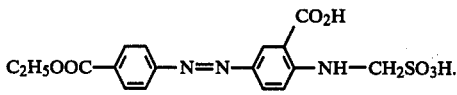

If then the protective group is split off at 70°-95° C. by means of acid (for example in about 80% strength formic acid), and the product is isolated in a conventional manner, 544 parts of the compound of the formula

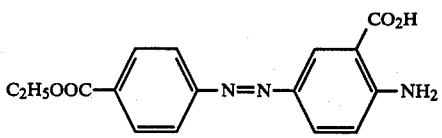

are obtained as a yellowish brown powder of melting point 210° C. The absorption maximum in dimethylformamide, at a concentrate of 0.01 part per 1,000 parts by volume of dimethylformamide, is at 413 nm. 289 parts of this product in 1,400 parts by volume of chloroform and 50 parts by volume of tetrahydrofuran are phosgenated in a conventional manner at 40°-50° C. After filtering off and drying, 301 parts of the compound of the formula

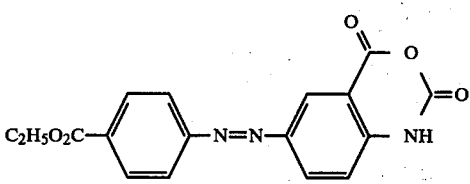

are obtained as a brown powder (absorption maximum in dimethylformamide: 419 nm).

158 parts of this product are added to a mixture of 700 parts of ethyl alcohol and 10 parts of triethylamine. The mixture is then stirred for 1½ hours at 50°-60° C., excess alcohol is distilled off as far as possible and after addition of water the product formed is isolated in a conventional manner. After drying, 150 parts of the diazo component of the formula

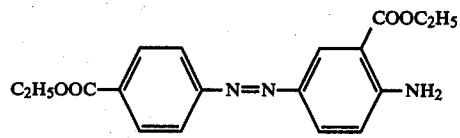

are obtained; this gives a pale yellow solution in dimethylformamide and has an absorption maximum of 406 nm.

EXAMPLE 8

34.6 parts of the compound of the formula

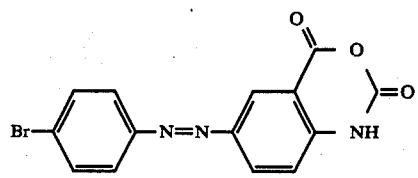

are stirred into 250 parts by volume of N-methylpyrrolidone. 8 parts of diethylamine are added at 50° C. and the resulting solution is stirred for 2 hours at 80° C. The reaction mixture is then precipitated by pouring onto ice water. The product which separates out, of the formula

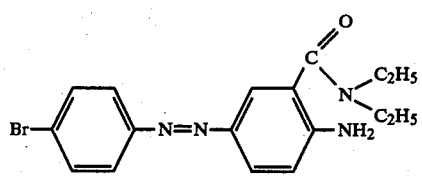

is isolated in a conventional manner. A yellow powder, melting at 135° C., is obtained.

EXAMPLE 9

13.6 parts of the compound of the formula

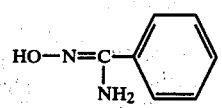

are dissolved in 100 parts by volume of water and 32 parts by volume of isobutanol and the mixture is heated to 50° C. 30.15 parts of the compound of the formula

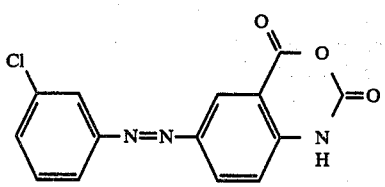

are then added and the mixture is stirred at 50°–70° C. When the elimination of $CO_2$ has ceased, the mixture is heated to 80° C. and 50% strength sodium hydroxide solution is added so that the pH of the mixture rises to 11–13. After a further 30 minutes' stirring the isobutanol is distilled off and the product which has precipitated is isolated by filtration. It is washed with water and dried, giving 31 parts of the compound of the formula

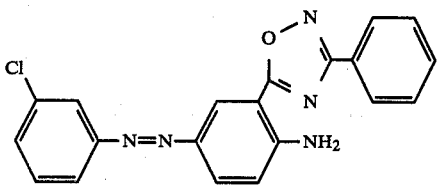

as a yellow powder, melting at 172°–175° C.

EXAMPLE 10

95 parts of the compound of the formula

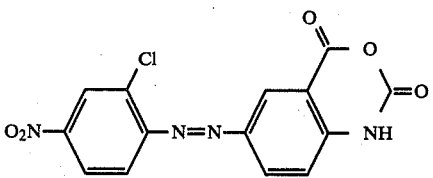

(a sandy-colored powder, melting/decomposition point 260°–265° C.) are reacted, by a method similar to that described in Example 4, with ethanol and triethylamine, and the mixture is worked up. 90 parts of a red powder, melting at 173° C., of the formula

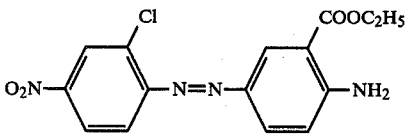

are obtained.

EXAMPLE 11

200 parts by volume of glacial acetic acid and 30 parts by volume of 30% strength hydrochloric acid are added to 20.8 parts of the compound of the formula

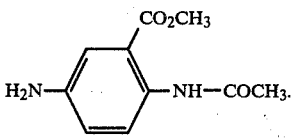

The mixture is cooled by adding 200 parts of ice, 33 parts by volume of a 23% strength sodium nitrite solution are then added and the diazotization is carried out for 3 hours at 0°–5° C. After excess nitrous acid has been destroyed, the diazonium salt solution is added dropwise to a solution, cooled to 0°–10° C., of 10 parts of phenol in 200 parts by volume of water and 50 parts of sodium acetate. After the mixture has been stirred overnight, the product which has formed, and has the formula

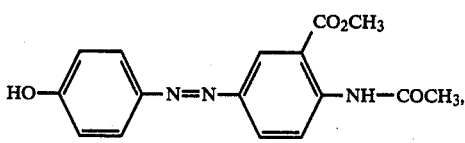

is isolated in a conventional manner and is then boiled for 4 hours in 300 parts by volume of methanol and 10 parts by volume of concentrated hydrochloric acid to split off the acetyl group. The aminoazo compound is isolated by cooling the reaction mixture in an ice-bath and filtering off the product which has precipitated. After washing and drying the latter, 13 parts of the compound of the formula

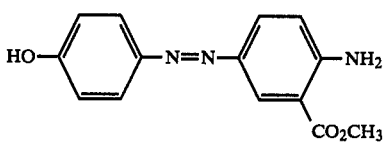

are obtained as a black powder, melting at 205°–212° C.

EXAMPLE 12

59 parts of the compound of the formula

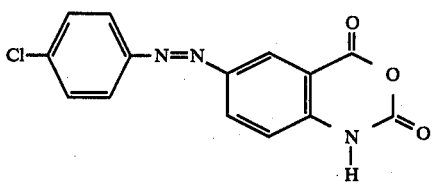

and 16 parts of acetic acid hydrazide in 100 parts of N-methylpyrrolidone are heated for 3 hours at 70° C. After the mixture has cooled it is diluted with 300 parts of water and the product is filtered off, washed with water and dried. 64 parts of the compound of the formula

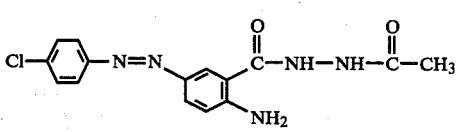

are obtained. 58 parts of this compound are introduced into 210 ml of 23% strength oleum at 0° C., 4 g of boric acid are also added, and the mixture is stirred for 1 hour at 5°–10° C. and then for 10 hours at 24° C. The reaction solution is then poured onto ice and the product is filtered off, washed with water and dried. 53 parts of the compound of the formula

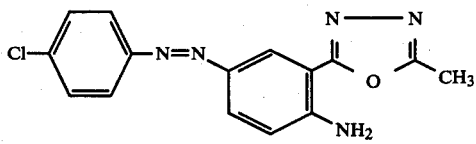

are obtained as a yellow crystalline powder of melting point 220°–223° C.

EXAMPLE 13

13 parts of P$_2$O$_5$ are added to 27 parts of the compound of the formula

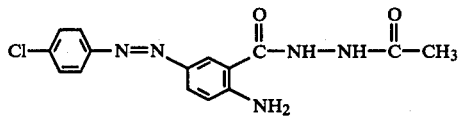

in 100 parts of N-methylpyrrolidone, and the mixture is stirred for 4 hours at 100° C. It is then diluted with 300 parts of water and the product is filtered off, washed and dried at 50° C. 25 parts of the compound of the formula

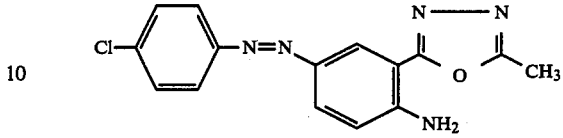

are isolated; melting point 220°–223° C.

The compounds characterized in the Tables which follow can also be prepared by a method similar to those described.

TABLE 1

| Example | A | R$^1$ | M.p. (°C.) | λmax. (nm) |
|---|---|---|---|---|
| 14 | 2,4,5-trichlorophenyl | CH$_3$ | 208–210 | 413 |
| 15 | " | CH$_2$CH(OCH$_3$)CH$_3$ | 126–128 | |
| 16 | 4-chloro-2-nitrophenyl | CH$_3$ | 185–187 | |
| 17 | 2,4-dichlorophenyl | CH$_2$CH(OCH$_3$)CH$_3$ | 103–105 | |
| 18 | 4-chloro-2-cyanophenyl | C$_{10}$H$_{21}$ | 49 | |
| 19 | 2,4-dichlorophenyl | CH$_2$CH$_2$O-phenyl | 139–141 | |

TABLE 1-continued

A—N=N—[benzene with CONH₂ and NH₂ groups]

| Example | A | R¹ | M.p. (°C.) | λmax. (nm) |
|---|---|---|---|---|
| 20 | 3,4-dichlorophenyl | CH₂CH(OCH₃)CH₃ | 101–104 | |
| 21 | 3-nitrophenyl | CH₂CHOCH₃ with CH₃ | 137–140 | |
| 22 | 4-chloro-2-methylphenyl | (CH₂)₃O(CH₂CH₂O)₂CH₃ | | 364 |
| 23 | 2,4-dichlorophenyl | C₆H₁₃(n) | 127–131 | |
| 24 | " | C₈H₁₇(i) | 88–92 | |
| 25 | " | CH₂CH(OCH₃)CH₃ | 121–124 | 409 |
| 26 | 2,4-dichlorophenyl | C₈H₁₇(i) | | 393 |
| 27 | 3-nitrophenyl | CH₃ | | 396 |
| 28 | " | C₃H₇(n) | 160–163 | 358, 398 |
| 29 | 3-chloro-4-nitrophenyl | " | | 433 |
| 30 | 4-nitrophenyl | CH₃ | 232 | 424 |

TABLE 1-continued

Structure: A—N=N—(benzene ring)—C(=O)NH$_2$ with NH$_2$ substituent

| Example | A | R$^1$ | M.p. (°C.) | λmax. (nm) |
|---|---|---|---|---|
| 31 | 3-Cl-4-(CH$_3$SO$_2$)-phenyl | C$_6$H$_{13}$(n) | | 416 |
| 32 | " | CH$_3$ | | 415 |
| 33 | 4-(CH$_2$=CH—CH$_2$SO$_2$)-phenyl | CH$_3$ | 136–138 | 360 shoulder, 403 |
| 34 | 2-NO$_2$-phenyl | CH$_3$ | 195–197 | 356 shoulder, 402 |
| 35 | 3-Cl-phenyl | CH$_2$CH(OH)CH$_3$ | | 391, shoulder 361 |
| 36 | 2-CN-phenyl | CH$_3$ | 210–213 | 363; 407.5 |
| 37 | " | C$_2$H$_5$ | 158–160 | |
| 38 | " | C$_3$H$_7$(n) | 128–130 | |
| 39 | 3-Cl-phenyl | CH$_2$CH(OCH$_3$)CH$_3$ | 97–99 | |
| 40 | 3,5-di-Cl-phenyl | " | 104–107 | |
| 41 | 2,4-di-Cl-phenyl | (CH$_2$)$_3$OCH$_2$-phenyl | | 408 |
| 42 | " | (CH$_2$)$_3$O(CH$_2$)$_2$O-phenyl | | 408 |

TABLE 1-continued

[Structure: A—N=N—benzene ring with CONH₂ and NH₂ groups]

| Example | A | R¹ | M.p. (°C.) | λmax. (nm) |
|---|---|---|---|---|
| 43 | 4-Cl-phenyl | 4-CH₃-phenyl | | 380 |
| 44 | " | 4-OCH₃-phenyl | | 382 |
| 45 | " | 4-Cl-phenyl | | 379 |
| 46 | " | CH₂CH=CH₂ | | 391 |
| 47 | " | phenyl | | 376 |
| 48 | 2-Cl-phenyl | cyclohexyl (H) | 102–106 | 392 |
| 49 | " | C₃H₁₃(n) | 77 | 355, 393 |
| 50 | 2-COOCH₃-phenyl | (CH₂)₃OC₂H₅ | 52 | |
| 51 | " | (CH₂)₃O(CH₂)₂OCH₃ | 30 | |
| 52 | 2-(phenyl-SO₂)-phenyl | (CH₂)₃O(CH₂CH₂O)₂C₄H₉(n) | liquid | |
| 53 | " | CH₂CH₂—N(pyrrolidinone) | 85 | |

If, in preparing the compounds listed in Table 1, cyclic amines are used instead of the amines employed in Table 1, the corresponding amides are obtained, for instance

| Example | | M.p. (°C.) |
|---|---|---|
| 54 | 2-amino-5-[(2-chlorophenyl)azo]benzoyl morpholine | 154–157 |
| 55 | 2-amino-5-[(2-chloro-4-methylsulfonylphenyl)azo]benzoyl piperazine | |
| 56 | 2-amino-5-[(2-cyanophenyl)azo]benzoyl pyrrolidine | |
| 57 | 2-amino-5-[(4-dimethylsulfamoylphenyl)azo]benzoyl piperazine | |
| 58 | 2-amino-5-[(3-chlorophenyl)azo]-4-methylbenzoyl morpholine | 163–166 |

Methods similar to those mentioned in Examples 1, 2, 5 and 9 may also be used to prepare, for example, the following azoanthranilic acid derivatives:

D—N=N—(benzene ring with COOH and NH₂)—

| D | Melting point (°C.) | λmax. (nm) |
|---|---|---|
| 2,4,5-trichlorophenyl | | 420 |
| 2,4,5-trichlorophenyl (isomer) | | 375 |
| 2,4-dichlorophenyl | 200–202 | 412 |

-continued

D–N=N–⟨phenyl with COOH and NH₂⟩

| D | Melting point (°C.) | λmax. (DMF) |
|---|---|---|
| 3,4-dichlorophenyl | | 401 |
| 2,5-dichlorophenyl | | 416 |
| 2,3-dichlorophenyl | 255–256 | 406 |
| 3,5-dichloro-4-nitrophenyl | 230–235 | 394 |
| 2-chloro-4-nitrophenyl | | 441 |
| 3-nitrophenyl | | 420 |
| 2-methoxy-4-nitrophenyl | | 409 |
| 2-methyl-4-nitrophenyl | | 433 |
| 2,4-dimethyl-...nitrophenyl | 232 | 424 |
| 4-chloro-2-methylphenyl | | 397 |
| 2,4-dibromo-5-methylphenyl | | 180 |
| 3-chloro-4-[(CH₃)₂N–SO₂]phenyl | | 410 (Iso-butanol) |

| D | Melting point (°C.) | λmax. (DMF) |
|---|---|---|
| 2,5-dichloro-4-[(CH₃)₂N–SO₂]phenyl | | 495 |
| 3,5-dichloro-4-[(CH₃)₂N–SO₂]phenyl | | 943 |
| 4-(phenylazo)phenyl | | 425 |
| 5-chloro-2-cyanophenyl | | 475 |
| 3-bromo-5-chloro-...-cyanophenyl | | 391 |
| 3,5-dibromo-4-cyanophenyl | 249–253 | |

-continued
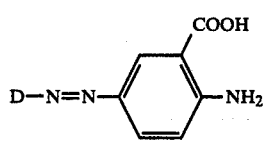
| | |
|---|---|
| 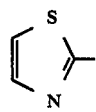 | 164-170 |
| 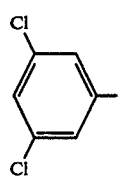 | 412 |
| 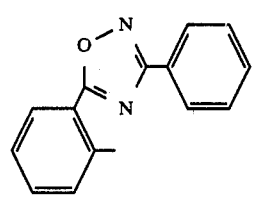 | 353 |
| 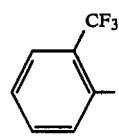 | |
| 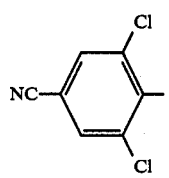 | |
| 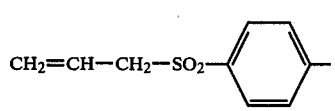 | |
| 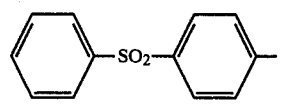 | |
| 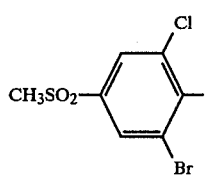 | |
-continued
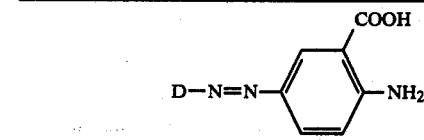
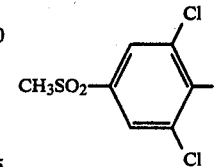
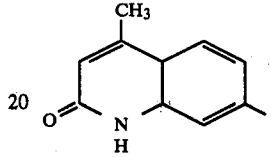
| D | Melting point (°C.) | λmax. (nm) |
|---|---|---|
| 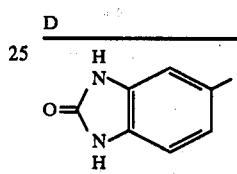 | | |
| 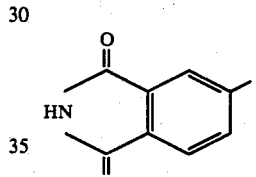 | | |
| 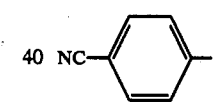 | | |
| 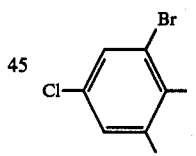 | | |
| 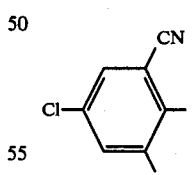 | | |
| 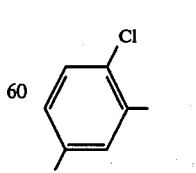 | | |

TABLE 2

Structure: A—N=N—[benzene ring with C(=O)—OR and NH₂ substituents]

| Example | A | R | M.p. (°C.) | λmax. (nm) |
|---|---|---|---|---|
| 59 | 4-Cl-C₆H₄ | CH₂CH₂CH(OCH₃)CH₃ | 103–104 | |
| 60 | " | C₆H₁₃(n) | 106–107 | |
| 61 | 2,5-diCl-C₆H₃ | C₆H₅ | 187–188 | 405 |
| 62 | 4-Cl-C₆H₄ | C₁₀H₂₁ | 67–70 | |
| 63 | 5-Cl-2-Br-3-CF₃-C₆H₂ | CH(CH₃)₂ | 113–17 | |
| 64 | 2-CF₃-C₆H₄ | CH₃ | 104–106 | |
| 65 | " | C₂H₅ | 97–99 | |
| 66 | " | C₄H₉(n) | 75–77 | |
| 67 | 4-Cl-2-CH₃-C₆H₃ | CH₃ | (sinters at 160–170) 190–195 | |
| 68 | 4-Cl-C₆H₄ | C₆H₁₃(i) | | |
| 69 | " | C₇H₁₅(n) | | |
| 70 | " | C₇H₁₅(i) | | |
| 71 | " | C₈H₁₇(n) | | |
| 72 | " | CH₂CH(C₂H₅)—C₄H₉(n) | | |
| 73 | " | | | |
| 74 | " | C₉H₁₉(n) | | |
| 75 | 2-Cl-C₆H₄ | C₁₀H₂₁(n) | 65–68 | |
| 76 | 2-CN-5-O₂N-C₆H₃ | CH₃ | 228 (decomp.) | 461 |
| 77 | 4-Cl-C₆H₄ | C₆H₅ | 188–192 | 375 |
| 78 | " | CH₂—C₆H₆ | | |
| 79 | " | CH₂CH₂C₆H₅ | | |
| 80 | " | (CH₂CH₂O)₂CH₃ | 62–64 | shoulder 365, 389 |

TABLE 2-continued

[Structure: A—N=N— attached to benzene ring with C(=O)—OR at top and NH₂]

| Example | A | R | M.p. (°C.) | λmax. (nm) |
|---|---|---|---|---|
| 81 | " | (CH₂CH₂O)₂C₂H₅ | 58–60 | |
| 82 | " | (CH₂CH₂O)₂C₄H₉(n) | | |
| 83 | " | (CH₂CH₂O)₃CH₃ | | |
| 84 | " | (CH₂CH₂O)₃C₄H₉(n) | | |
| 85 | " | (CH₂CH₂O)₄C₄H₉(n) | | |
| 86 | " | —⌬—CH₃ | 152–154 | |
| 87 | Cl—⌬— | CH₃-substituted phenyl | | |
| 88 | " | —⌬—OCH₃ | | |
| 89 | " | —⌬—Cl | 205–210 | |
| 90 | " | CH₂CH₂O—⌬ | | |
| 91 | " | CH₂CH₂NHCOCH₃ | | |
| 92 | " | CH₂CH₂CH₂NHCOCH₃ | | |
| 93 | " | —⌬—CH₂CH₂CN | | |
| 94 | " | CH₂CH₂OH | | |
| 95 | " | (methyl-naphthyl) | | |

If instead of the radicals A shown in Table 2, the following radicals, for example, are employed:

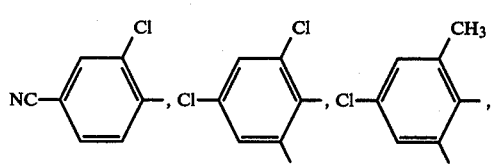

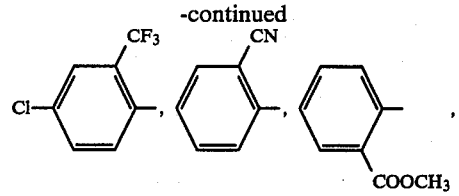

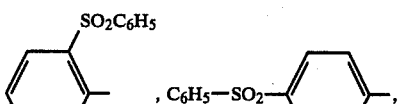

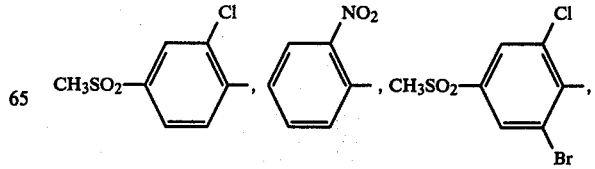

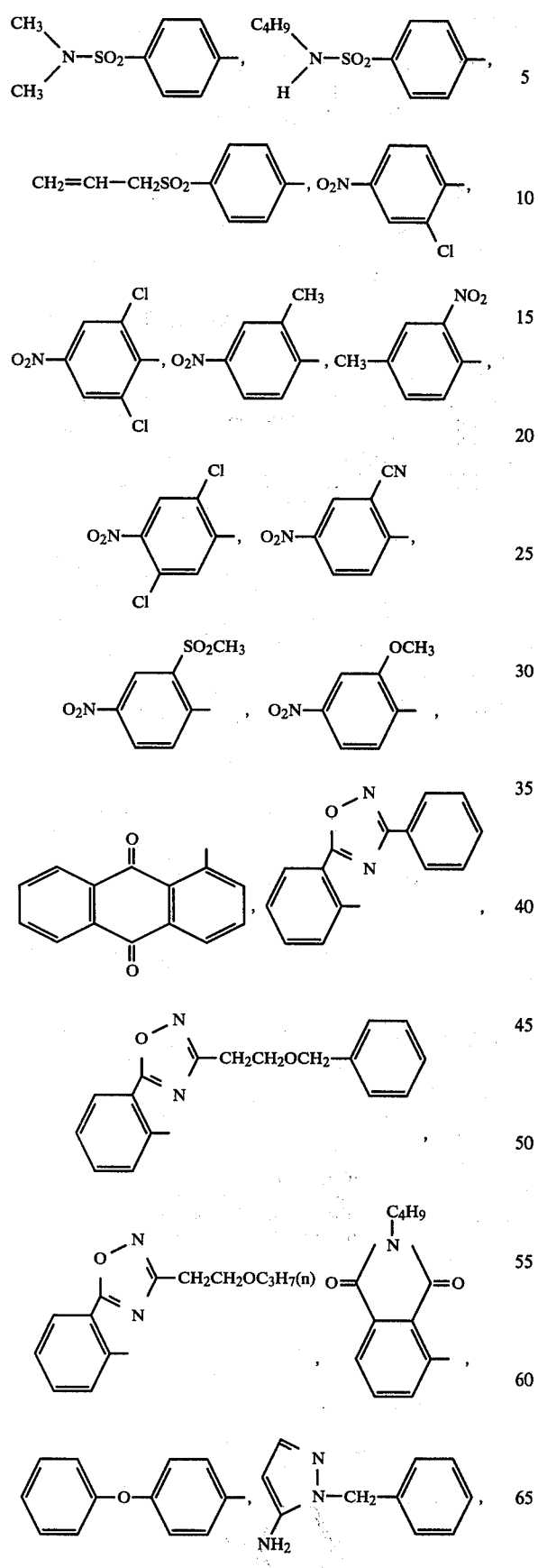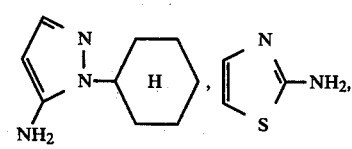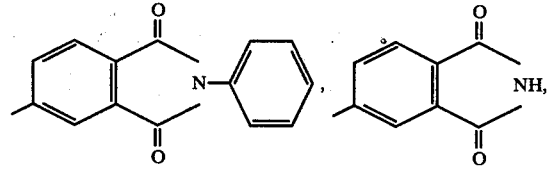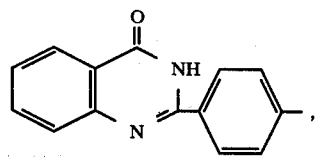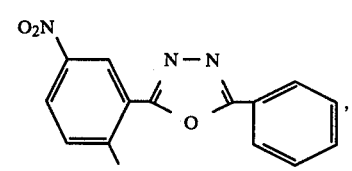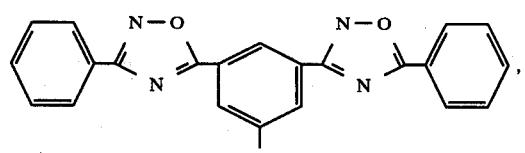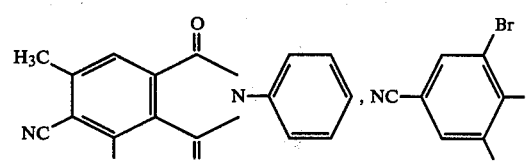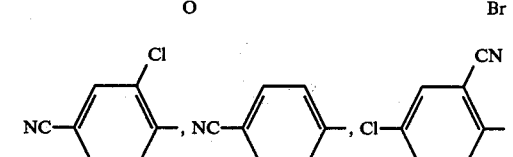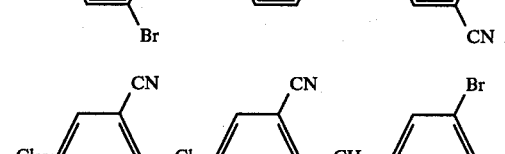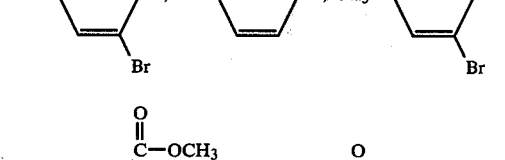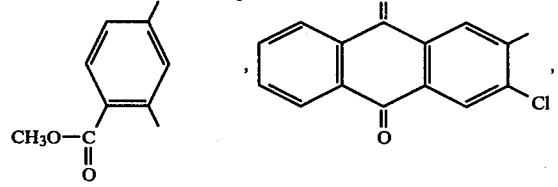

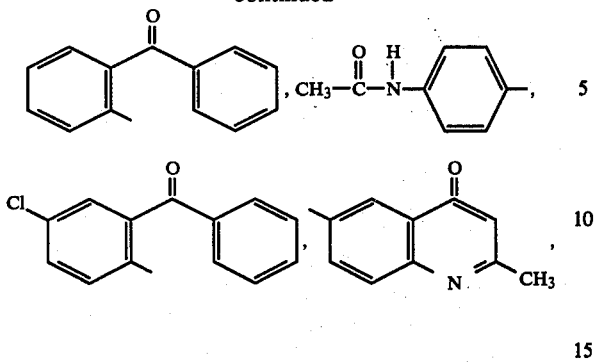
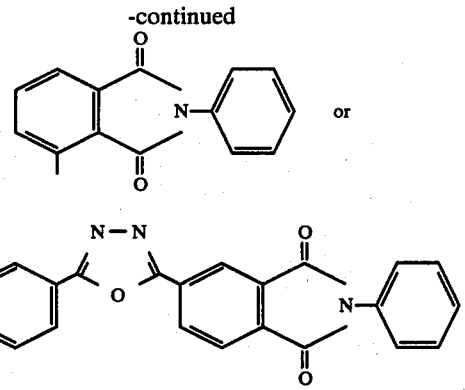
and the procedures described in the Examples are followed, the corresponding diazo components are obtained.
TABLE 3
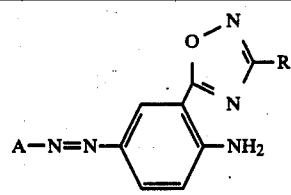
| Example | A | R | M.p. (°C.) | λmax. (nm) |
|---|---|---|---|---|
| 87 | 2-Cl-C6H4- | $CH_3$ | | 360 |
| 88 | " | $C_2H_5$ | | 362 |
| 89 | " | $C_6H_{13}$ | | |
| 90 | " | $CH_2OCH_3$ | | 359 |
| 91 | " | $CH_2CH_2OCH_3$ | | |
| 92 | " | $(CH_2)_2OC_2H_5$ | | |
| 93 | " | $(CH_2)_2OC_3H_7(n)$ | | 362 |
| 94 | " | $(CH_2)_2OC_3H_7(i)$ | | 362 |
| 95 | 3-Cl-C6H4- | $(CH_2)_2O(CH_2)_2OCH_3$ | | 360 |
| 96 | " | $(CH_2CH_2O)_3CH_3$ | | |
| 97 | " | $(CH_2CH_2O)_2C_2H_5$ | | |
| 98 | " | $(CH_2CH_2O)_2C_4H_9(n)$ | | |
| 99 | " | $(CH_2CH_2O)_3C_4H_9(n)$ | | |
| 100 | " | C6H5- | | 400 |
| 101 | " | 4-CH3-C6H4- | | |
| 102 | " | 4-Cl-C6H4- | | 398 |

TABLE 3-continued
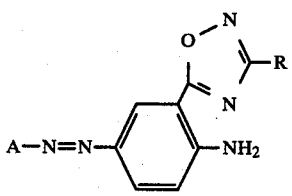
| Example | A | R | M.p. (°C.) | λmax. (nm) |
|---|---|---|---|---|
| 103 | " | 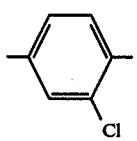 | | |
| 104 | " | CH₂CH₂SO₃H | | |
| 105 | 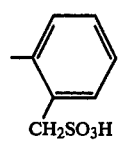 | CH₂SO₃H | | 353 |
| 106 | " | 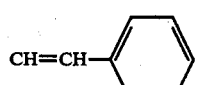 | | 373 |
| 107 | " | 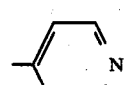 | | |
| 108 | " | 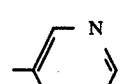 | | |
| 109 | " | 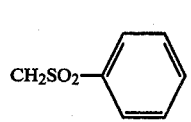 | | |
| 110 | " | 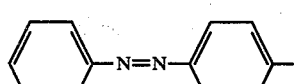 | | |
| 111 | " | CH₂—C₆H₅ | | |
| 112 | 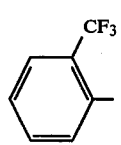 | CH₃ | | |
| 113 | " | (CH₂)₂OC₃H₇ | | |
| 114 |  | (CH₂)₂OC₃H₇ | | 368 |

TABLE 3-continued

[Structure: A—N=N—benzene(NH2)—oxadiazole-R]

| Example | A | R | M.p. (°C.) | λmax. (nm) |
|---------|---|---|------------|------------|
| 115 | CH₂=CH—CH₂—SO₂—C₆H₄— | " | | |
| 116 | 3-Cl-4-(CH₃SO₂)—C₆H₃— | " | | |
| 117 | C₄H₉(n)-SO₂—C₆H₄— | " | | |
| 118 | 2-methyl-phenyl with oxadiazole-phenyl group | C₆H₅ | | |

TABLE 4

[Structure: A—N=N—benzene(NH2)—oxadiazole-R]

| Example | A | R | M.p. (°C.) | λmax. (nm) |
|---------|---|---|------------|------------|
| 119 | 2-Cl-C₆H₄— | CH₃ | | |
| 120 | " | C₂H₅ | | |
| 121 | " | C₃H₇ | | 364, 420 |
| 122 | " | CH₂OCH₃ | | 360, 418 |
| 123 | " | CH₂OC₆H₅ | | |
| 124 | " | C₆H₅ | | |
| 125 | 3-Cl-C₆H₄— | CH₃ | | |
| 126 | " | C₂H₅ | | |
| 127 | " | C₃H₇ | | |
| 128 | " | CH₂OCH₃ | | |
| 129 | " | C₆H₅ | | |
| 130 | 4-Cl-C₆H₄— | C₂H₅ | | |
| 131 | " | C₃H₇ | | |
| 132 | " | CH₂OCH₃ | | |
| 133 | " | C₆H₅ | | |
| 134 | 2-CF₃-C₆H₄— | " | | |
| 135 | 2-COOCH₃-C₆H₄— | " | | 250–254 |
| 136 | 2-SO₂C₆H₅-C₆H₄— | " | | |

EXAMPLE 137

11.0 parts of the compound of the formula

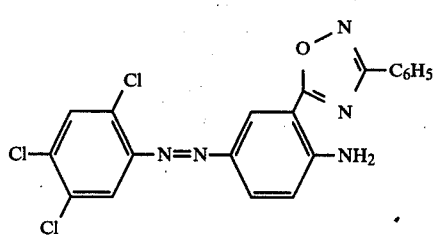

are stirred for 1 hour, at 40° C., with 200 parts by volume of water, 5 parts by volume of 16% strength hydrochloric acid and 0.5 part of a wetting agent. 6.4 parts of bromine are then added dropwise in the course of 2 hours at 40°-60° C., and the mixture is stirred for 2 hours at 80° C. and then cooled to room temperature. It is diluted with 200 parts by volume of water and the product is filtered off, washed with water and dried, giving 13 parts of a compound, of melting point 230°-235° C., having the formula

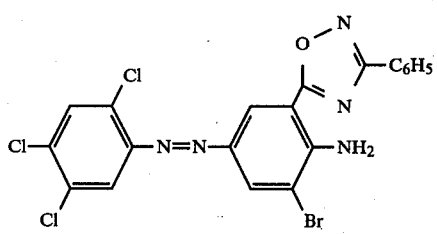

EXAMPLE 138

15.0 parts of the aminoazo compound of the formula

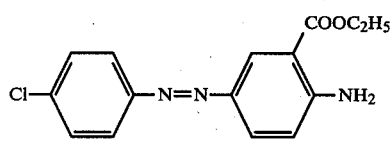

are brominated with 8.8 parts of bromine by a method similar to that described in Example 137; 18 parts of the diazo component of the formula

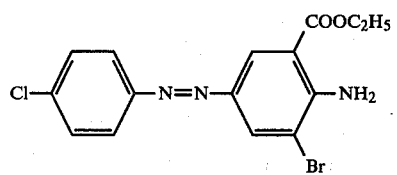

are obtained; melting point 133°-135° C.

Chlorination by known methods gives the corresponding chlorine compounds.

TABLE

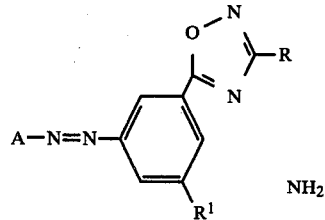

| Example | A | R¹ | R | M.p. (°C.) | λmax. (nm) |
|---|---|---|---|---|---|
| 139 | 2-Cl-C₆H₄- | H | CH₂CH₂OCH₂ | 102–104 | 361 |
| 140 | " | Br | C₆H₅ | | 373 |
| 141 | 4-Cl-C₆H₄- | " | " | | 372 |
| 142 | " | H | 2-SO₃H-C₆H₄- | | 373 |
| 143 | 4-Br-C₆H₄- | H | " | | 385 |
| 144 | 4-Cl-2-CH₃-C₆H₃- | H | " | 194 | 350 |
| 145 | " | Cl | " | | 351 |
| 146 | 2,4-Cl₂-C₆H₃- | " | " | | 412 |
| 147 | " | Br | " | | 380 |
| 148 | 2,4-Cl₂-C₆H₃- | H | 2-Cl-C₆H₄- | | 376, 403 |
| 149 | " | H | 3-CH₃-C₆H₄- | | 397 |
| 150 | 2,4,6-Cl₃-C₆H₂- | H | C₆H₅ | | 370 |
| 151 | 2,4,5-Cl₃-C₆H₂- | H | " | 249–251 | 362, 419 |
| 152 | 2-NO₂-C₆H₄- | Br | " | | 376 |

TABLE-continued

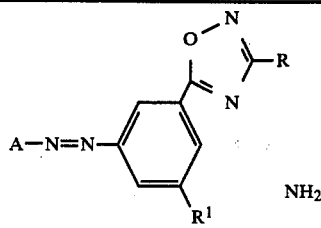

| Example | A | R¹ | R | M.p. (°C.) | λmax. (nm) |
|---|---|---|---|---|---|
| 153 | 3-NO₂-phenyl | H | " | 246–290 | |
| 154 | 2-CN-phenyl | H | " | decomp. >220 | 373 |
| 155 | 2-CF₃-phenyl | H | " | 176–179 | |
| 156 | 2,4-diCl-phenyl | H | " | 246–249 | |
| 157 | 3-Cl-phenyl | H | " | 246–249 | |
| 158 | 4-Cl-phenyl | H | " | 240–241 | |
| 159 | CH₂=CH—CH₂SO₂-phenyl | H | " | | |
| 160 | 2-NO₂-phenyl | Br | " | 137–140 | |
| 161 | 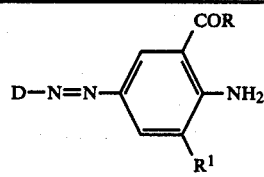 | H | " | 263–265 | |
| 162 | 4-Cl-3-CN-phenyl | | | | |

TABLE $$\begin{array}{c} \text{COR} \\ \text{D—N=N—} \bigcirc \text{—NH}_2 \\ \text{R}^1 \end{array}$$

| Example | D | R | R¹ | Melting Point (°C.) | λmax. (nm) |
|---|---|---|---|---|---|
| 163 | 2,4,6-triCl-phenyl | OC₂H₄OCH₃ | Br | 128–131 | 361 |
| 164 | 4-Cl-phenyl | morpholino (—N(CH₂CH₂)₂O) | H | 188 | 398 |
| 165 | " | piperidino | H | 160–164 | |
| 166 | " | OCH₃ | Br | | 356,5 |

TABLE-continued $$D-N=N-\underset{R^1}{\underset{|}{\bigcirc}}-\underset{NH_2}{\overset{COR}{|}}$$

| Example | D | R | R$^1$ | Melting Point (°C.) | λmax. (nm) |
|---------|---|---|-------|---------------------|------------|
| 167 | 4-Cl-2-NO$_2$-phenyl | " | " | 189–192 | 405; 355 shoulder |
| 168 | 2,4-diCl-phenyl | " | " | | 357; 403 |
| 169 | 2-Br-phenyl | OCH$_3$ | H | | 353; 400 |
| 170 | " | OC$_2$H$_5$ | H | | 354; 397 |
| 171 | phenyl | OC$_3$H$_7$ | H | | 353; 396 |
| 172 | 2-CF$_3$-phenyl | OC$_6$H$_{13}$(n) | H | 50–52 | |
| 173 | 4,6-dimethyl-2-hydroxyquinolinyl | OCH$_3$ | H | | |
| 174 | 3-NO$_2$-phenyl | OC$_4$H$_9$ | H | 139–141 | 355; 396,5 |
| 175 | " | OCH$_2$CHCH$_3$ | H | 137–140 | |
| | | $\quad$ $\overset{|}{O}$CH$_3$ | | | |
| 176 | 5-methylbenzimidazol-2(3H)-one | OCH$_3$ | H | 221–225 | |

TABLE

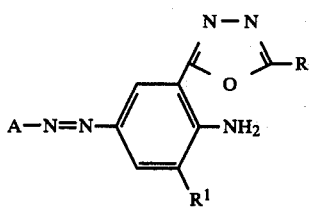

| Example | A | R$^1$ | R | M.p. (°C.) | $\lambda_{max.}$ (nm) |
|---|---|---|---|---|---|
| 177 | Cl, Cl, Cl-phenyl | H | CH$_3$ | 202–205 | |
| 178 | " | H | C$_6$H$_5$ | | 361, 420 |
| 179 | " | H | CH$_3$ | 181–185 (decomp.) | |
| 180 | Cl, Cl-phenyl | H | " | | |
| 181 | " | Br | C$_6$H$_5$ | | |
| 182 | " | H | C$_6$H$_5$ | | |
| 183 | O$_2$N-phenyl- | " | " | | |
| 184 | NO$_2$-phenyl- | " | " | | |
| 185 | C$_2$H$_5$OOC-phenyl- | " | " | | |

EXAMPLE 186

10 parts of CuCN are added to 33 parts of the diazo component of the formula

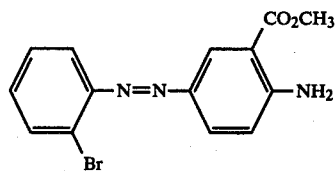

in 300 parts of dimethylformamide at 80°–100° C. The mixture is stirred for 1 hour at 120°–130° C. and then cooled to 20° C., and 65 parts of aqueous ammonia solution of about 25% strength are run in. After stirring the mixture for 30 minutes, 100 parts of water are added dropwise and the precipitate suspension is then stirred for 30 minutes and filtered off. To purify the filter residue, the latter is stirred with 100 parts of methanol, filtered off and dried at 80° C. 37 parts of the yellow compound of the formula

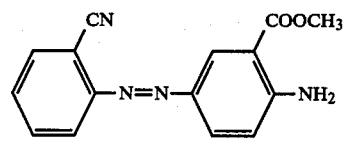

are obtained; melting point 208°–210° C.

EXAMPLE 187

40 parts of the compound of the formula

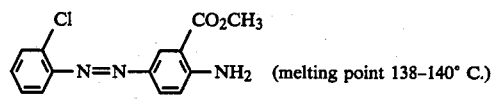 (melting point 138–140° C.)

are added, a little at a time, with stirring, to 105 parts of 23% strength oleum at 15°–25° C. The sulfonation mixture is then stirred for 6 hours at 40° C., cooled to room temperature and poured out onto 400 parts of ice. The precipitate obtained is neutralized to pH 4–6 with sodium hydroxide solution or sodium acetate. The product which has precipitated, of the formula

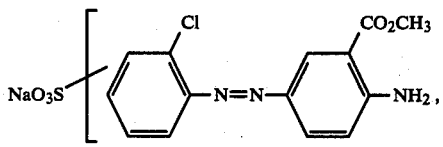

is filtered off, washed with a small amount of water and dried. 42 parts of a yellowish brown powder, which gives a yellow solution in water, are obtained. The ultraviolet absorption spectrum, recorded with a Bittman ACTA III spectrophotometer, shows a maximum at 394 nm (pH 5, in water). According to a thin layer chromatogram, the diazo component is a single compound. It decomposes on heating to above 270° C.

The compounds listed in the Table which follows can be synthesized by a procedure similar to that described in Example 186. The replacement of bromine by cyano as a rule takes place very easily. In the replacement of chlorine by cyano, which as a rule takes place less easily, N-methylpyrrolidone is used instead of dimethylformamide and the reaction temperature is raised, if necessary to 170°–180° C.

TABLE
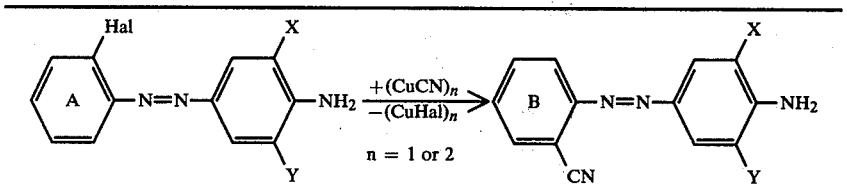
n = 1 or 2
| Example | A (Hal) | B (CN) | X | Y | M.p. (°C.) | $\lambda_{max}$ (nm) |
|---|---|---|---|---|---|---|
| 188 | 2-Br-phenyl | 2-CN-phenyl | $CO_2C_2H_5$ | H | 158–160 | |
| 189 | " | " | $CO_2C_3H_7$ | H | 128–130 | 351, 409 |
| 190 | " | " | $CO_2C_6H_5$ | H | | |
| 191 | " | " | $CO_2C_6H_{13}(n)$ | H | | |
| 192 | " | " | 3-methyl-1,2,4-oxadiazol-5-yl | H | | |
| 193 | " | " | 2,5-dimethyl-1,3,4-oxadiazole (N=N) | H | | 373 |
| 194 | " | " | CON(morpholino) | H | | |
| 195 | 2,6-dibromo-4-methylphenyl | 2,6-dicyano-4-methylphenyl | " | H | | |
| 196 | 2-Br-4-$NO_2$-phenyl | 2-CN-4-$NO_2$-phenyl | $COOC_2H_5$ | H | | 462 |
| 197 | " | " | $COOC_4H_9$ | H | | |
| 198 | " | " | 3-phenyl-1,2,4-oxadiazol-5-yl | H | | |
| 199 | " | " | $COOCH_3$ | Br | | |
| 200 | " | " | 3-methyl-1,2,4-oxadiazol-5-yl | Br | | |

TABLE-continued

Structure:
Ar(A, Hal) — N=N — Ar(X, Y, NH₂) + (CuCN)ₙ / −(CuHal)ₙ → Ar(B) — N=N — Ar(X, Y, NH₂) with CN
n = 1 or 2

| Example | A (Hal) | B (CN) | X | Y | M.p. (°C) | $\lambda_{max}$ (nm) |
|---|---|---|---|---|---|---|
| 201 | 2-Br, 4-Cl, 6-Br phenyl | 3-CN, 5-Cl, 6-CN phenyl | " | Br | | |
| 202 | 3-Cl, 4-NC, 6-Br phenyl | 3-Cl, 4-NC, 6-CN phenyl | " | H | | |
| 203 | " | " | " | Br | | |
| 204 | " | " | " | Cl | | |
| 205 | 2-Cl phenyl | 2-CN phenyl | CO₂CH₃ | H | 208–210 | |
| 206 | " | " | CO₂C₂H₅ | Cl | | |
| 207 | 3-Br, 4-NC, 6-Br phenyl | 3-CN, 4-NC, 6-CN phenyl | oxadiazolyl-C₆H₅ (with CH₃) | H | | |
| 208 | " | " | CO₂C₆H₁₃(n) | " | | |
| 209 | " | " | CO₂C₈H₁₇(i) | " | | |

A procedure similar to that described in Examples 1, 2, 5 and 9 may also be used to prepare, for example, the following azo-isatoic anhydrides:

D—N=N—[aryl with C(=O)—O—C(=O)—NH ring (isatoic anhydride)]

| D | M.p. (°C) | $\lambda_{max}$ (nm) in dimethylformamide |
|---|---|---|
| 2,4,5-trichlorophenyl | 320–324 | 457 |

-continued
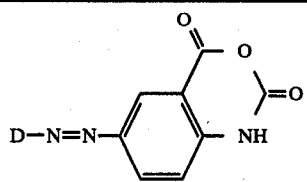
| D | M.p. (°C.) | λ_max (nm) in dimethylformamide |
|---|---|---|
| 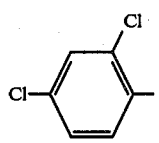 | 305 (decomp.) | 360, 418 (two maxima) |
| 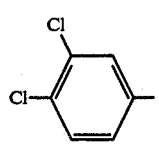 | 268–271 | |
| 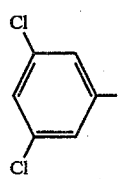 | 286–291 | |
| 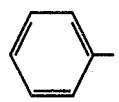 | | 391, 5 |
| 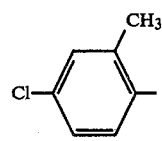 | | 355, 419 |
| 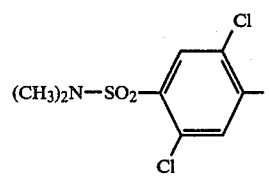 | 163–169 | 375, 474 |
| 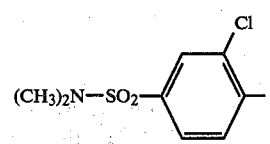 | 176–180 | |
| 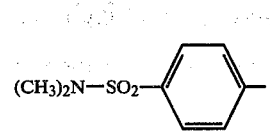 | 275–280 | |
| 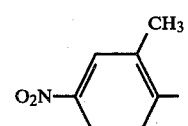 | 268–270 | 369, 460 |
-continued
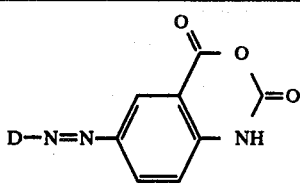
| D | M.p. (°C.) | λ_max (nm) in dimethylformamide |
|---|---|---|
| 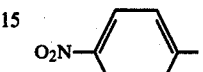 | | 366, 465 |
| 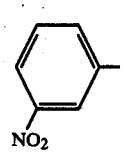 | 301–304 | |
| 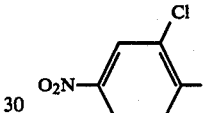 | | 375, 484 |
| 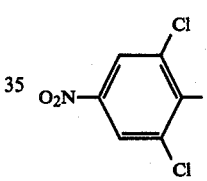 | 280–284 | |
| 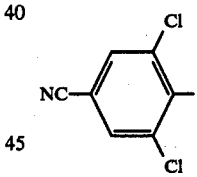 | | |
| 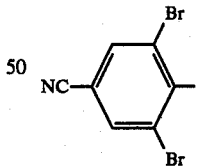 | | |
| 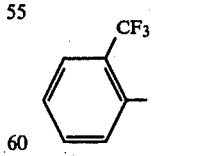 | 278–284 | |
| 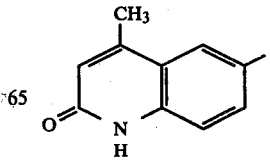 | | |

-continued

| D | M.p. (°C.) | λ_max (nm) in dimethylformamide |
|---|---|---|

[Structure: D—N=N—benzene with CO-O-C=O and NH forming ring]

| D | M.p. (°C.) | λ_max (nm) in dimethylformamide |
|---|---|---|

[Structure: D—N=N—benzene with CO-O-C=O and NH forming ring (isomer)]

[Structure: benzimidazol-2(3H)-one with H, N, O=C, N, H]

[Structure: phenyl-N=N-tolyl]

[Structure: 4-methyl-7-methyl-quinolin-2(1H)-one with CH₃, O, N-H]

[Structure: 2-methoxy-4-nitro-toluene; O₂N, OCH₃] — 295–299

[Structure: o-methyl-benzonitrile; CN]

[Structure: CH₂=CH—CH₂—SO₂—phenyl-methyl] — 265–270

[Structure: phthalimide-methyl; HN with two C=O]

[Structure: 5-chloro-2-methyl-benzonitrile; Cl, CN] — 265 (decomp.)

[Structure: 4-chloro-3-methyl-benzonitrile; Cl, CN]

[Structure: 4-bromo-3-methyl-benzene diazonium; Br, CN₂]

We claim:
1. An aminoazo compound of the general formula:

$$A-N=N-\underset{R}{\overset{X}{\underset{\phantom{Z}}{\text{Ar}}}}-Z$$

wherein:
A is the radical of a diazo component or coupling component,
R is a radical of the formula:

[Structure: isoxazoline ring with N=C(R³)—O—N and R¹]

wherein:
R¹ is unsubstituted or substituted alkyl, alkenyl, cycloalkyl or aryl,
R³ is hydrogen or a radical R¹;
Z is amino, or
X is hydrogen, chlorine, bromine, methoxy, ethoxy, propoxy, butoxy, phenoxy, methyl, ethyl, propyl, butyl, acetylamino, dimethylamino, diethylamino, carboxyl or -NO₂.

2. A compound as claimed in claim 1, of the formula:

$$D-N=N-\underset{\phantom{Z}}{\overset{R}{\text{Ar}}}-Z$$

wherein
D is the radical of a diazo component and
Z and R have the stated meanings.

* * * * *

UNITED STATES PATENT AND TRADEMARK OFFICE
CERTIFICATE OF CORRECTION

PATENT NO. : 4,424,155
DATED : January 3, 1984
INVENTOR(S) : Walter Kurtz et al

It is certified that error appears in the above-identified patent and that said Letters Patent is hereby corrected as shown below:

On the title page item /30/ should read
--[30] Foreign Application Priority Data Mar 15, 1980 [DE] Fed. Rep. of Germany .....3010104 --

Signed and Sealed this

Twenty-seventh Day of March 1984

[SEAL]

Attest:

GERALD J. MOSSINGHOFF

Attesting Officer    Commissioner of Patents and Trademarks